United States Patent
Corbett et al.

(10) Patent No.: US 11,833,314 B2
(45) Date of Patent: Dec. 5, 2023

(54) DUAL LUMEN SHEATH FOR ARTERIAL ACCESS

(71) Applicant: ABIOMED, Inc., Danvers, MA (US)

(72) Inventors: Scott C. Corbett, Danvers, MA (US);
Glen R. Fantuzzi, Danvers, MA (US);
John Murphy, Danvers, MA (US);
Frank Kirchhoff, Aachen (DE); David Brousseau, Danvers, MA (US);
Thorsten Siess, Aachen (DE)

(73) Assignee: ABIOMED, INC., Danvers, MA (US)

( * ) Notice: Subject to any disclaimer, the term of this patent is extended or adjusted under 35 U.S.C. 154(b) by 70 days.

(21) Appl. No.: 17/351,671

(22) Filed: Jun. 18, 2021

(65) Prior Publication Data
US 2021/0361926 A1 Nov. 25, 2021

Related U.S. Application Data

(60) Continuation of application No. 16/907,533, filed on Jun. 22, 2020, now abandoned, which is a division of
(Continued)

(51) Int. Cl.
*A61M 25/01* (2006.01)
*A61M 60/135* (2021.01)
(Continued)

(52) U.S. Cl.
CPC ...... *A61M 25/0102* (2013.01); *A61M 60/135* (2021.01); *A61M 60/148* (2021.01);
(Continued)

(58) Field of Classification Search
CPC .......... A61M 25/0102; A61M 25/0045; A61M 25/0662; A61M 60/148; A61M 60/135;
(Continued)

(56) References Cited

U.S. PATENT DOCUMENTS

| 4,137,916 A | 2/1979 | Killman et al. |
| 4,180,068 A | 12/1979 | Hansen et al. |

(Continued)

FOREIGN PATENT DOCUMENTS

| CN | 102481398 A | 5/2012 |
| JP | S61199867 A | 9/1986 |

(Continued)

OTHER PUBLICATIONS

Office Action for Japanese Application No. 2021-034186 dated Dec. 16, 2021 (10 pages).
(Continued)

*Primary Examiner* — Tammie K Marlen
(74) *Attorney, Agent, or Firm* — Botos Churchill IP Law LLP (57) ABSTRACT

A sheath assembly for the insertion of a percutaneous pump includes a tubular sheath body dimensioned for insertion into a blood vessel through a vessel aperture. The tubular sheath body includes a wall having a proximal end portion, a distal end portion, a longitudinal axis, an outer surface, an inner surface defining a first lumen substantially parallel to the longitudinal axis, and a second lumen disposed within the wall between the inner surface and the outer surface and extending from the proximal end portion to the distal end portion. The first lumen is dimensioned to allow passage of a portion of the percutaneous pump, and the second lumen is dimensioned for passage of a guidewire. A stylet is removably positioned to substantially occlude the second lumen. The stylet has a proximal end releasably secured to the sheath assembly.

20 Claims, 4 Drawing Sheets

Related U.S. Application Data application No. 14/827,741, filed on Aug. 17, 2015, now Pat. No. 10,737,008.

(51) Int. Cl.
  *A61M 60/148* (2021.01)
  *A61M 60/422* (2021.01)
  *A61M 60/216* (2021.01)
  *A61M 25/00* (2006.01)
  *A61M 25/02* (2006.01)
  *A61M 25/06* (2006.01)

(52) U.S. Cl.
  CPC ........ *A61M 60/216* (2021.01); *A61M 60/422* (2021.01); *A61M 25/0045* (2013.01); *A61M 25/0662* (2013.01); *A61M 2025/0003* (2013.01); *A61M 2025/0008* (2013.01); *A61M 2025/0018* (2013.01); *A61M 2025/0047* (2013.01); *A61M 2025/0286* (2013.01)

(58) Field of Classification Search
  CPC .............. A61M 60/422; A61M 60/216; A61M 2025/0003; A61M 2025/0008; A61M 2025/0018; A61M 2025/0047; A61M 2025/0286
  See application file for complete search history.

(56) References Cited

U.S. PATENT DOCUMENTS

| | | |
|---|---|---|
| 4,643,711 A | 2/1987 | Bates |
| 4,699,611 A | 10/1987 | Bowden |
| 4,988,365 A | 1/1991 | Sternberger et al. |
| 4,995,863 A | 2/1991 | Nichols et al. |
| 5,139,486 A | 8/1992 | Moss |
| 5,234,425 A | 8/1993 | Fogarty et al. |
| 5,304,142 A | 4/1994 | Liebl et al. |
| 5,320,611 A | 6/1994 | Bonutti et al. |
| 5,395,341 A | 3/1995 | Slater |
| 5,397,310 A | 3/1995 | Chu et al. |
| 5,407,430 A | 4/1995 | Peters |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,653,697 A | 8/1997 | Quiachon et al. |
| 5,911,702 A | 6/1999 | Romley et al. |
| 5,935,122 A | 8/1999 | Fourkas et al. |
| 5,971,993 A | 10/1999 | Hussein et al. |
| 6,197,016 B1 | 3/2001 | Fourkas et al. |
| 6,338,730 B1 | 1/2002 | Bonutti et al. |
| 6,428,556 B1 | 8/2002 | Chin |
| 6,613,038 B2 | 9/2003 | Bonutti et al. |
| 6,692,462 B2 | 2/2004 | MacKenzie et al. |
| 6,814,715 B2 | 11/2004 | Bonutti et al. |
| 7,025,746 B2 | 4/2006 | Tal |
| 7,722,567 B2 | 5/2010 | Tal |
| 7,988,614 B2 | 8/2011 | Ben |
| 8,317,773 B2 | 11/2012 | Appling et al. |
| 8,509,916 B2 | 8/2013 | Byrd et al. |
| 8,597,277 B2 | 12/2013 | Lenker et al. |
| 8,672,888 B2 | 3/2014 | Tal |
| 8,758,402 B2 | 6/2014 | Jenson et al. |
| 2002/0107506 A1 | 8/2002 | McGuckin et al. |
| 2004/0116848 A1 | 6/2004 | Gardeski et al. |
| 2005/0149105 A1 | 7/2005 | Leeflang et al. |
| 2006/0135981 A1 | 6/2006 | Lenker et al. |
| 2006/0287574 A1 | 12/2006 | Chin |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2009/0192435 A1 | 7/2009 | Gregersen |
| 2009/0240202 A1 | 9/2009 | Drasler et al. |
| 2011/0040241 A1 | 2/2011 | Wang et al. |
| 2011/0319728 A1 | 12/2011 | Petisce et al. |
| 2012/0065579 A1 | 3/2012 | Cully et al. |
| 2012/0296152 A1 | 11/2012 | Reichenbach et al. |
| 2013/0131718 A1 | 5/2013 | Jenson et al. |
| 2013/0317438 A1 | 11/2013 | Ellingwood et al. |
| 2013/0317481 A1 | 11/2013 | Ellingwood et al. |
| 2013/0331639 A1 | 12/2013 | Campbell et al. |
| 2014/0121448 A1 | 5/2014 | Smith et al. |
| 2015/0051635 A1 | 2/2015 | Kravik et al. |
| 2015/0141738 A1 | 5/2015 | Toellner et al. |
| 2016/0008573 A1 | 1/2016 | Loesener et al. |
| 2016/0066948 A1 | 3/2016 | Ellingwood et al. |
| 2016/0220358 A1 | 8/2016 | Wilson et al. |
| 2016/0354583 A1 | 12/2016 | Ellingwood et al. |
| 2017/0056063 A1 | 3/2017 | Ellingwood et al. |
| 2017/0281908 A1 | 10/2017 | Ellingwood et al. |
| 2019/0255245 A1 | 8/2019 | Kelly et al. |

FOREIGN PATENT DOCUMENTS

| | | |
|---|---|---|
| JP | H0663143 A | 3/1994 |
| JP | 2003508161 A | 3/2003 |
| JP | 2003275318 A | 9/2003 |
| JP | 2005287670 A | 10/2005 |
| JP | 2007202901 A | 8/2007 |
| JP | 2012231969 A | 11/2012 |
| JP | 2013539664 A | 10/2013 |
| WO | 2012165429 A1 | 12/2012 |

OTHER PUBLICATIONS

Office Action for Indian Application No. 201817008179 dated Oct. 8, 2021 (5 pages).

Office Action for Korean Application No. 10-2018-7007479, dated Oct. 18, 2021.

Third Party Submission Under 37 CFR 1.290 in U.S. Appl. No. 16/907,533 dated Nov. 20, 2020, 41 pages.

Office Action from Israeli Patent Application No. 285740, dated Dec. 21, 2021, 8 pp.

Extended European Search Report for corresponding EP Application No. 22 161 299.7 dated Jun. 22, 2022,(10 pages).

International Search Report (PCT/US2016/047421) dated Nov. 4, 2016.

Japanese Office Action for corresponding Japanese Patent Application No. 2018-508747 dated Aug. 24, 2020 (6 pages).

Supplementary EP Search Report EP 16837779.4 dated Mar. 5, 2019.

Reverdin, Stephanie , et al., "Bridge to Transplantation with the TandemHeart", TandemHeart in Chronic Aortic Dissection with Shock vol. 35, No. 3, 2008, Nov. 3, 2008, 340-341.

Office Action for corresponding AU Application No. 2021204533 dated Aug. 29, 2022 (3 pages).

Office Action for Canadian Application No. 2,995,707 dated Jan. 11, 2023 (7 pp.).

DUAL LUMEN SHEATH FOR ARTERIAL ACCESS

CROSS-REFERENCE TO RELATED APPLICATION

This application is a continuation of U.S. patent application Ser. No. 16/907,533, filed Jun. 22, 2020, now abandoned, which is a divisional of U.S. patent application Ser. No. 14/827,741, filed Aug. 17, 2015, now U.S. Pat. No. 10,737,008, the disclosures of all of which are incorporated herein by reference in their entirety.

BACKGROUND

A blood pump, such as a percutaneous intracardiac blood pump assembly, is introduced in the heart to deliver blood from the heart into an artery. When deployed in the heart, a blood pump assembly pulls blood from the left ventricle of the heart and expels blood into the aorta, or pulls blood from the right ventricle and expels blood into the pulmonary artery. Blood pump assemblies are introduced surgically or percutaneously during a cardiac procedure through the vascular system. In one common approach, pump assemblies are inserted by a catheterization procedure through the femoral artery using a peel-away introducer sheath.

The peel-away introducer sheath is inserted into the femoral artery through an arteriotomy to create an insertion path for the pump assembly. A portion of the pump assembly is then advanced through an inner lumen of the introducer and into the artery. Once the pump assembly has been inserted, the peel-away introducer sheath can be peeled away. A repositioning sheath can then be advanced over the pump assembly and into the arteriotomy. Replacing the introducer sheath with the repositioning sheath can prevent blood clot formation in the introducer sheath, prevent or reduce bleeding from the arteriotomy, and allow blood to flow through the femoral artery to the leg. But after the introducer sheath is removed, wire access to the artery is lost. Loss of the guidewire access makes it more difficult to close the vessel after the procedure or to exchange devices in the arteriotomy.

To maintain guidewire access, some physicians leave the peel-away introducer sheath in the arteriotomy for extended durations of time. The extended presence of the peel-away sheath in the arteriotomy can reduce recoil of the arteriotomy and thus increase the final diameter of the arteriotomy. This increase in diameter can increase the risk of bleeding through the arteriotomy once the peel-away introducer sheath is finally removed. Furthermore, the extended presence of the peel-away sheath in the artery can reduce perfusion through the femoral artery, thereby increasing the risk of ischemia.

Additionally, clinicians sometimes choose to monitor a patient's arterial pressure during the catheterization procedure. Measurement of the patient's arterial pressure often requires the placement of an additional catheter. The presence of the additional catheter can add bulk to the operating area and requires entry into the arterial system via another access point.

SUMMARY

Systems, methods, and devices for an improved dual lumen repositioning sheath are presented. The dual lumen sheath can be inserted into an arteriotomy after an introducer sheath is removed to maintain guidewire access to the arteriotomy. The dual lumen sheath includes a first lumen sized for passage of a portion of a percutaneous pump and a second lumen sized for the insertion of a guidewire. The second lumen receives a guidewire to be inserted into the arteriotomy alongside a percutaneous pump to maintain guidewire access to the insertion path of the percutaneous pump. By maintaining guidewire access using the second lumen of the dual lumen sheath, the introducer sheath can be removed from a patient without losing the guidewire access. This allows the physician to remove the introducer sheath earlier in a procedure (e.g., 1 hour, 30 minutes, 10 minutes, 5 minutes, or immediately after successful insertion of the percutaneous pump), which allows the blood vessel aperture to recoil to a smaller diameter compared to the diameter it would assume if the introducer sheath were left in the patient for longer. For example, a recoil of 2 to 3 French (0.667 mm to 1 mm) may be achieved if the introducer sheath is removed before the blood vessel aperture permanently relaxes to the larger diameter of the introducer sheath.

The dual lumen sheath also includes a removable stylet that is inserted into the second lumen to reduce the risk of blood clot formation in the second lumen during the medical procedure. Maintaining the patency of the second lumen is particularly helpful in procedures having a longer duration (e.g., six hours or longer). The removable stylet may be reversibly coupled to the dual lumen sheath during insertion of the dual lumen sheath into the arteriotomy and during the medical procedure. Before the percutaneous pump is removed, the stylet is removed from the second lumen to allow insertion of the guidewire through the second lumen. In some implementations, the patency of the guidewire port is maintained using a drug or nondrug coating applied to the second lumen. In certain implementations, the second lumen is flushed with a liquid at a controlled rate to maintain patency.

In some embodiments, the dual lumen sheath also includes a rotatable connection to a stabilizing structure (e.g., suture pads). The rotatable connection allows the outlet of the second lumen at the distal end of the sheath to be rotated away from an arterial wall. This can facilitate the insertion of the guidewire by allowing the guidewire to be inserted in a direction not directly against the arterial wall, thereby reducing the friction associated with insertion of the guidewire. Additionally, the rotation allows the port for the second lumen to lie flat against the patient when the second lumen is not in use.

The second lumen provides a number of possible other advantages. For example, it also allows arterial pressure to be transduced without the need for an additional catheter. Transducing the pressure can allow a physician to determine when the dual lumen sheath has been inserted to a sufficient depth. If the second lumen is used to transduce pressure, the rotation of the guidewire outlet enabled by the rotatable connection to the stabilizing structure can improve the reliability of the pressure measurement by keeping the outlet of the second lumen off of the arterial wall. Additionally, the second lumen can be used to determine the depth of insertion without a pressure transducer. For example, the depth of insertion can be determined by observing the onset of blood flow through the second lumen ("bleedback"), which is indicative of penetration into the arteriotomy. Regardless of whether a pressure transducer or a bleedback indicator is used, depth markings can be disposed on an outer surface of the sheath to facilitate measurement of the depth of insertion. The depth markings may be radio-opaque. The measurement of the depth of the arteriotomy relative to the patient's skin can facilitate the subsequent use of certain vessel closure tools which may require such a measurement.

In one aspect, a sheath assembly for the insertion of a percutaneous pump includes a tubular sheath body dimensioned for insertion into a blood vessel through a vessel aperture. The tubular sheath body includes a wall having a proximal end portion, a distal end portion, a longitudinal axis, an outer surface, an inner surface defining a first lumen substantially parallel to the longitudinal axis, and a second lumen disposed within the wall between the inner surface and the outer surface and extending from the proximal end portion to the distal end portion. The first lumen is dimensioned to allow passage of a portion of the percutaneous pump, and the second lumen is dimensioned for passage of a guidewire. A stylet is removably positioned to substantially occlude the second lumen.

In certain implementations, the stylet has a proximal end configured to be releasably secured to the sheath assembly. In some implementations, the length of the stylet is substantially equal to the length of the second lumen. In certain implementations, the stylet is radio-opaque or includes radio-opaque marker bands to show the distance of the sheath in the blood vessel. In certain implementations, the sheath assembly also includes a hub coupled to the proximal end portion of the sheath body and including a first port in fluid communication with the first lumen, and a second port in fluid communication with the second lumen, wherein the second port is configured to secure the proximal end of the stylet. The sheath body may be dimensioned to be introduced through a percutaneous access site of about 20 Fr (6.67 mm) or less (e.g., 19 Fr, 18 Fr, 17 Fr, 16 Fr, 15 Fr, 14 Fr, 13 Fr, 12 Fr, 10 Fr, 9 Fr, 8 Fr, 6 Fr, or less).

In some implementations, the distal end portion of the sheath body is tapered and includes a tapered surface extending to a distal end face, the distal end face being substantially orthogonal to the longitudinal axis of the sheath body. In certain implementations, the second lumen has an outlet extending through the tapered surface of the distal end portion of the sheath body. The second lumen may be coated with an antithrombogenic agent. In some implementations, the outer surface of the wall of the tubular sheath body includes a hydrophilic coating or any other suitable coating to prevent tissue adhesion. In certain implementations, the outer surface of the wall includes markings for determining a depth of insertion, for example with evenly spaced markings on the outer surface of the wall.

In certain implementations, the sheath assembly of claim also includes a stabilizing structure rotatably coupled to the tubular sheath body. The stabilizing structure may be rotatable about the longitudinal axis. In some implementations, the stabilizing structure includes a feature configured for suturing to a patient. The stabilizing structure may include a pair of suture wings, each wing having a plurality of ribs for securing sutures.

In another aspect, a method for maintaining guidewire access includes inserting a sheath into a blood vessel through a percutaneous insertion path and along a portion of a percutaneous pump, wherein the sheath has a first lumen and a second lumen, maintaining the sheath in the vessel for more than 6 hours while preventing blood clot formation from occluding the second lumen, and inserting a guidewire through the second lumen into the percutaneous insertion path after the more than 6 hours.

In some implementations, maintaining the patency includes inserting a stylet into the second lumen for more than 6 hours, and removing the stylet before inserting the guidewire. In certain implementations, maintaining the patency includes flushing the second lumen with purge fluid. In some implementations, the method the method also includes removing the sheath while maintaining the guidewire in the percutaneous insertion path. In certain implementations, the method also includes inserting a percutaneous tool over the guidewire into the percutaneous insertion path after the sheath is removed. In some implementations, the method also includes coupling a sensor to the proximal inlet of the second lumen and transducing arterial pressure at the distal outlet of the second lumen using the sensor. In certain implementations, the method also includes rotating the sheath relative to a support structure when the pressure measurement indicates that the distal outlet is occluded by an arterial wall. In some implementations, the method also includes determining a depth of insertion from the pressure measurement. The depth of insertion may be determined using depth markers disposed on an outer surface of the sheath.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, method, and devices described herein, certain illustrative embodiments will be described. Although the embodiments and features described herein are specifically described for use in connection with a percutaneous blood pump system, it will be understood that all the components and other features outlined below may be combined with one another in any suitable manner and may be adapted and applied to other types of cardiac therapy and cardiac assist devices, including balloon pumps, cardiac assist devices implanted using a surgical incision, and the like.

The systems, methods, and devices described herein provide a dual lumen sheath having a first lumen sized for passage of a portion of a percutaneous pump and a second lumen sized for insertion of a guidewire. The second lumen is positioned to allow the guidewire to be inserted into the insertion path of the percutaneous pump. This allows guidewire access to the insertion path to be maintained even after the percutaneous pump and dual lumen sheath are retracted. The guidewire access allows one or more other tools (e.g., a vessel closure tool) to be subsequently inserted into the same insertion path to facilitate vessel closure or any other medical procedures involving guidewire access. Because the second lumen enables a physician to maintain the guidewire access after the introducer sheath is removed, the physician can remove the introducer sheath earlier in a medical procedure. Earlier removal of the introducer sheath allows the insertion path to recoil to a smaller diameter, thereby reducing the risk of bleeding through the access site.

The systems, methods, and devices described herein also include a stylet that maintains the patency of the second lumen. The stylet is used to occlude the second lumen when the second lumen is not being used for insertion of a guidewire or for pressure measurement. For example, the removable stylet may be positioned within the second lumen during insertion of the dual lumen sheath into the arteriotomy and during the operation of the percutaneous pump. Before the percutaneous pump is removed, the stylet is removed from the second lumen to allow insertion of the guidewire through the second lumen. The occlusion of the second lumen with the stylet can impede blood clot formation in the second lumen during medical procedures having a long duration (e.g., six hours or greater). This allows the second lumen to remain accessible during and after the medical procedure, for example to provide a path for insertion of the guidewire before removing the percutaneous pump. In some implementations, blood clot formation is prevented using a drug or nondrug coating applied to the second lumen. In certain implementations, blood clot formation is impeded by flushing the second lumen with a liquid at a controlled rate.

The dual lumen sheath may also include a rotatable connection to a stabilizing structure (e.g., suture wings). The rotatable connection allows the outlet of the second lumen at the distal end of the sheath to be rotated away from an arterial wall. This can facilitate the insertion of the guidewire by allowing the guidewire to be inserted in a direction not directly against the arterial wall, thereby reducing the friction associated with insertion of the guidewire. Additionally, the rotation allows the port for the second lumen to lie substantially flat against the patient when the second lumen is not in use.

The second lumen can also establish fluid communication between a guidewire port and the interior of the blood vessel. This can allow arterial pressure measurement (e.g., by a pressure transducer) during a procedure without the use of a separate catheter. Measuring the arterial pressure can allow a physician to detect when the dual lumen sheath has been inserted to a sufficient depth into the vessel. The rotation of the guidewire outlet enabled by the rotatable connection to the stabilizing structure can improve the reliability of the pressure measurement by keeping the outlet of the second lumen off of the arterial wall.

Figure 1:
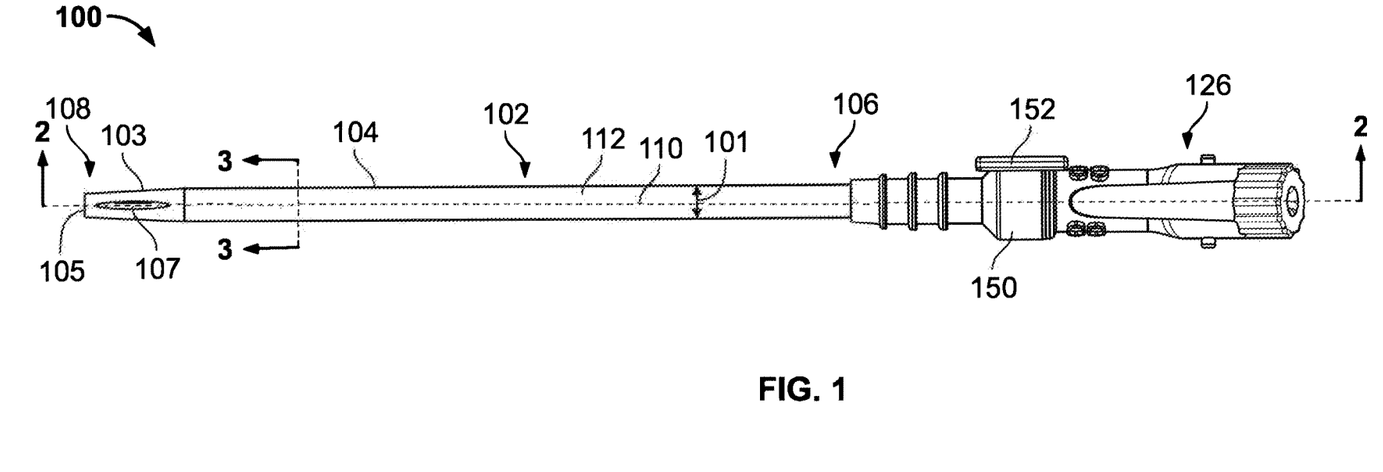
FIG. 1 shows a top view of an illustrative dual lumen sheath for arterial access.
Figure 2:
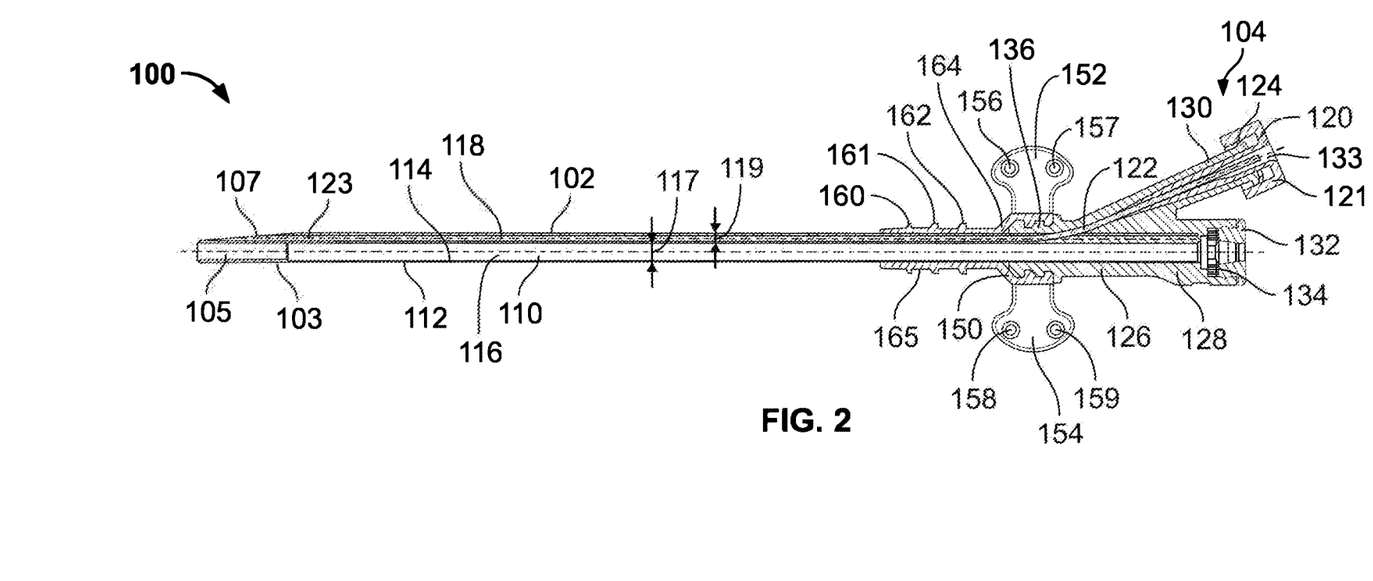
FIG. 2 shows a lateral section view of the dual lumen sheath of FIG. 1.
Figure 3:
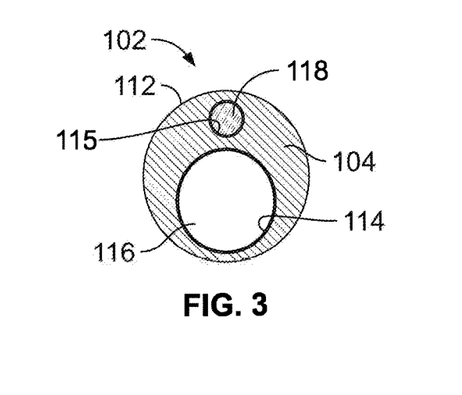
FIG. 3 shows a transverse cross section of the distal portion of the dual lumen sheath of FIG. 1.

FIG. 1 shows an illustrative dual lumen sheath assembly 100 for maintaining arterial access, according to certain implementations. FIG. 2 shows a lateral section view of the sheath assembly 100 taken along section line 2-2, and FIG. 3 shows a transverse cross-section of a distal portion of the sheath assembly 100 taken along section line 3-3. The sheath assembly 100 includes a tubular sheath body 102, a stylet 120, a hub 126, and a stabilizing structure 150. The tubular sheath body 102 is dimensioned for insertion into a blood vessel through a vessel aperture. In some implementations, the tubular sheath body 102 is dimensioned for insertion into a femoral artery through an arteriotomy. The majority of the tubular sheath body 102 may have a substantially uniform outer diameter 101 of about 10 Fr, 11 Fr, 12 Fr, 13, Fr, 14 Fr, 15 Fr, 16 Fr, 17 Fr, 20 Fr, or any other suitable diameter. The tubular sheath body may be dimensioned to be introduced through a percutaneous access site of about 20 Fr (6.67 mm) or smaller (e.g., 19 Fr, 18 Fr, 17 Fr, 16 Fr, 15 Fr, 14 Fr, 13 Fr, 12 Fr, 10 Fr, 9 Fr, 8 Fr, 6 Fr, or less). The tubular sheath body may have a length of about 80 mm, 100 mm, 120 mm, 140 mm, 160 mm, or any other suitable length. Additionally, the tubular sheath body 102 may be made of a flexible material, such as polyether block amides or any other suitable polymer, to reduce the stress on the blood vessel aperture.

The tubular sheath body 102 includes a wall 104, a proximal end portion 106, a distal end portion 108, a longitudinal axis 110, an outer surface 112, a first inner surface 114, a second inner surface 115, a first lumen 116, and a second lumen 118. The distal end portion 108 of the tubular sheath body 102 includes a tapered surface 103, a first outlet 105 in fluid communication with the first lumen 116, and a second outlet 107 in fluid communication with the second lumen 118. The tapered surface 103 has an outer diameter graduated from 11 Fr to 15 Fr (3.667 mm to 5 mm). The graduation in the tapered surface 103 may permit the sheath to be inserted to a variable depth as necessary to plug the gap between the percutaneous pump and the insertion site.

The outer surface 112 of the tubular sheath body 102 may be coated with a hydrophilic coating to ease insertion of the tubular sheath body 102 into the arteriotomy. A hydrophilic coating can also prevent adhesions to the blood vessel wall. Such adhesions could damage the vessel if the sheath is removed after having been in the blood vessel for an extended period of time (e.g., many days). The risk of adhesion to the blood vessel wall can increase as the duration of a procedure increases. In some embodiments, the outer surface 112 of the tubular sheath body 102 includes depth markings. The depth markings may be pad printed or laser etched onto the outer surface 112. In certain implementations, the depth markings are radio-opaque. The depth markings may be in centimeters, inches, millimeters, or any other suitable unit of measurement or combination thereof.

The first inner surface 114 of the tubular sheath body defines the first lumen 116. The first lumen 116 is dimensioned to allow passage of a portion of the percutaneous pump. The first lumen 116 extends from the proximal end portion 106 of the tubular sheath body 102 to the distal end portion 108, substantially parallel to the longitudinal axis 110. The second lumen 118 is disposed within the wall 104 between the inner surface 114 and the outer surface 112. The second lumen 118 extends from the proximal end portion 106 of the tubular sheath body 102 to the distal end portion 108, offset from and substantially parallel to the longitudinal axis 110. The second lumen 118 is dimensioned for the passage of a guidewire and is defined by the second inner surface 115 (as shown in FIG. 3). The second inner surface 115 may include a drug or non-drug coating to prevent blood clot formation in the second lumen 118. In some implementations, the second inner surface is coated with heparin. The second lumen 118 terminates at the second outlet 107 formed in the tapered surface 103. The second outlet 107 is adjacent to the first outlet 105 of the first lumen 116. As a result, if a guidewire is inserted through the second lumen 118, the guidewire enters the insertion path of the percutaneous pump (not shown) passing through the first lumen 116. Thus, the second lumen 118 may be used to maintain or regain guidewire access to the insertion path of a percutaneous pump inserted through the first lumen 116. This allows guidewire access to the insertion path to be maintained even after an introducer sheath is removed. The guidewire access allows one or more other tools to be subsequently inserted into the same insertion path to facilitate vessel closure or any other medical procedures involving guidewire access. For example, the guidewire access may permit the subsequent insertion of a vessel closure tool or a micro pressure measurement catheter (e.g., MILLAR Mikro-Tip® pressure catheter). A micro pressure measurement catheter may allow measurement of pressure in the left ventricle or any other suitable pressure. Furthermore, since the second lumen enables a physician to maintain guidewire access after the introducer sheath is removed, the physician can remove the introducer sheath earlier. Earlier removal of the introducer sheath allows the vessel aperture to recoil to a smaller diameter, thereby reducing the risk of bleeding through the access site. Additionally, since the second outlet 107 is offset from the longitudinal axis 110, rotating the tubular sheath body 102 allows the position of the second outlet 107 to be adjusted. This can allow a user to keep the second outlet 107 off of a blood vessel wall to ease insertion of a guidewire or to increase the accuracy of an arterial pressure measurement.

The tubular sheath body 102 is connected at its proximal end portion 106 to the hub 126. The hub 126 includes a first port 128, a second port 130, second port threads 131, and a bearing 136. The second port 130 is connected to the second lumen 118 so that a guidewire can be inserted through the second port 130 into the second lumen 118 and out of the second outlet 107. When a guidewire is not in the second lumen 118, the stylet 120 can be inserted into the second port 130 to seal the second lumen 118 (as shown in FIGS. 1, 2, and 3). The stylet 120 includes a head 121, a stylet body 122, a rounded end 123, and threads 126. The stylet body 122 is sized to substantially occlude the second lumen 118 when the stylet 120 is inserted into the second lumen 118. In some implementations, the stylet body 122 is made of a formable or ductile material, such as a metal. This may allow the stylet to be formed, either during the medical procedure or before, into a shape that reduces stress on the vessel aperture. In certain implementations, the stylet 120 is radio-opaque or includes radio-opaque marker bands to show the depth of the tubular sheath body 102 in a blood vessel. The threads 124 of the stylet head 121 reversibly couple with the second port threads 131 to hold the stylet 120 within the second lumen 118. When the stylet head 121 is reversibly coupled to the second port 130, the stylet head 121 forms a liquid tight seal across the second port 130, which prevents the leakage of blood out of the blood vessel. In certain implementations, in place of the stylet 120, a pressure bag is connected to the second port 130 using the threads 131. The pressure bag can be used to flush the second lumen 118 with a fluid to maintain the patency of the second lumen 118. An infusion pump may be used in combination with the pressure bag to regulate the flow rate of liquid into the patient. For example, the flow rate may be limited to 1 mL/hr, 2 mL/hr, 5 mL/hr, 10 mL/hr, or any other suitable flow rate. In some implementations, a pressure measuring device is connected to the second port 130 to measure pressure within the vessel 10. This pressure measurement can be used to determine when the second port 130 has been inserted sufficiently deep into the blood vessel aperture. For example, when a pressure about equal to arterial pressure is measured at the second port 130, the second outlet 107 may be in fluid communication with the blood vessel. The pressure measurement can also be used to monitor arterial pressure in the patient's blood vessel during a medical procedure. This may allow an arterial pressure measurement to be taken without the use of an additional catheter, which may reduce the amount of equipment necessary in the potentially crowded operating area.

The first port 128 of the hub 126 allows the passage of the percutaneous pump (not shown). The first port 128 includes a cap 132 and a seal 134. The cap 132 snaps into the first port 128 to hold the seal 134 against the first port 128. The cap 132 and seal 134 together act as a hemostatic valve and form a liquid tight seal between the percutaneous pump and the first port 128. The seal 134 is formed of an elastomer, such as silicone, so that it can flex to seal around a portion of the percutaneous pump.

The hub 126 is coupled to the stabilizing structure 150 by the bearing 136. The stabilizing structure 150 includes wings 152 and 154, suture holes 156-159, ribs 160-162, and a bearing surface 164 that mates with the bearing 136. The mating of the bearing surface 164 of the stabilizing structure 150 with the bearing 136 of the hub 126 allows rotation of the hub 126 relative to the stabilizing structure 150. As discussed above, this rotation allows the tubular sheath body 102 to be rotated such that the second outlet 107 is oriented away from a vessel wall. Additionally, this rotation allows the second port 130 to lie flat against a patient when the second port 130 is not in use. The suture holes 156-159 allow the wings 152 and 154 to be sutured to a patient to stabilize the sheath assembly 100. While only four suture holes 156-159 are shown, any suitable number of suture holes may be used. The stabilizing structure 150 is also designed to be easily attached to a vascular graft with umbilical tape or sutures. This feature is beneficial during axillary insertions or any other insertions which require pump placement through a vascular graft. Additionally, in some implementations, the stabilizing structure 150 is coupled to a patient using ribs 160-162. For example, sutures may be wrapped around the outer surface 165 of the stabilizing structure between the ribs 160-162. When sutures are wrapped around the outer surface 165 in such a manner, the ribs 160-162 prevent the sutures from sliding off of the outer surface 165 along the longitudinal axis 110. In certain implementations, other stabilizations devices, such as surgical tape, a STATLOCK® stabilization device (Bard Access Systems, Inc., Salt Lake City, Utah), or any other suitable adhesive stabilization device, may be coupled to the stabilizing structure 150 around the ribs 160-162.

Figure 4:
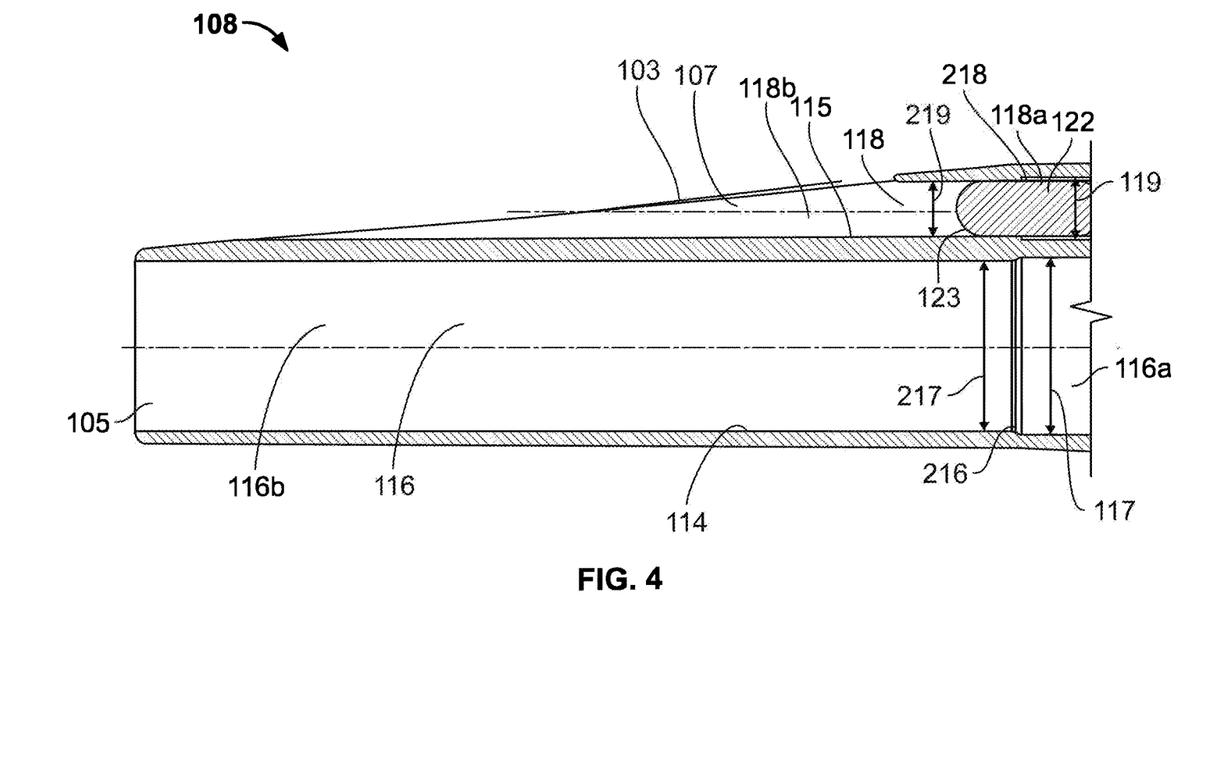
FIG. 4 shows a detailed section view of a distal portion of the dual lumen sheath of FIG. 1.

FIG. 4 shows a detailed section view of the distal portion 108 of the dual lumen sheath assembly 100 of FIGS. 1, 2, and 3. The distal portion 108 includes the tapered surface 103, the first outlet 105, the second outlet 107, and distal portions of the stylet body 122, the first lumen 116, and the second lumen 118. The first lumen 116 includes a proximal section 116a having an inner diameter 117, a distal section 116b having an inner diameter 217 which is less than the inner diameter 117, and a restriction 216 therebetween. The inner diameter 117 is about 13 Fr (4.333 mm), and the inner diameter 217 is about 9 Fr (3 mm). The restriction 216 allows the distal section 116b of the first lumen 116 to form a tighter fit with the percutaneous pump to prevent or reduce blood leakage without causing unacceptably high friction in the proximal section 116a. Similar to the first lumen 116, the second lumen 118 includes a proximal section 118a having a diameter 119, a distal section 118b having a diameter 219 that is less than the diameter 119, and a restriction 218 therebetween. The diameter 119 is about 1.1 mm and the diameter 219 is about 1 mm. The restriction 218 allows a tighter fit between the stylet body 122 and the second lumen 118 at the distal section 118a to reduce blood ingress, while allowing a clearance in the proximal section 118b to reduce friction. The friction between the second lumen 118 and the stylet body 122 is further reduced by the rounding of the end 123 of the stylet body 122. The rounded end 123 is located adjacent to the second outlet 107 when the stylet 120 is fully inserted into the second lumen 118, thereby preventing or reducing blood ingress into the second lumen 118.

Figure 5:
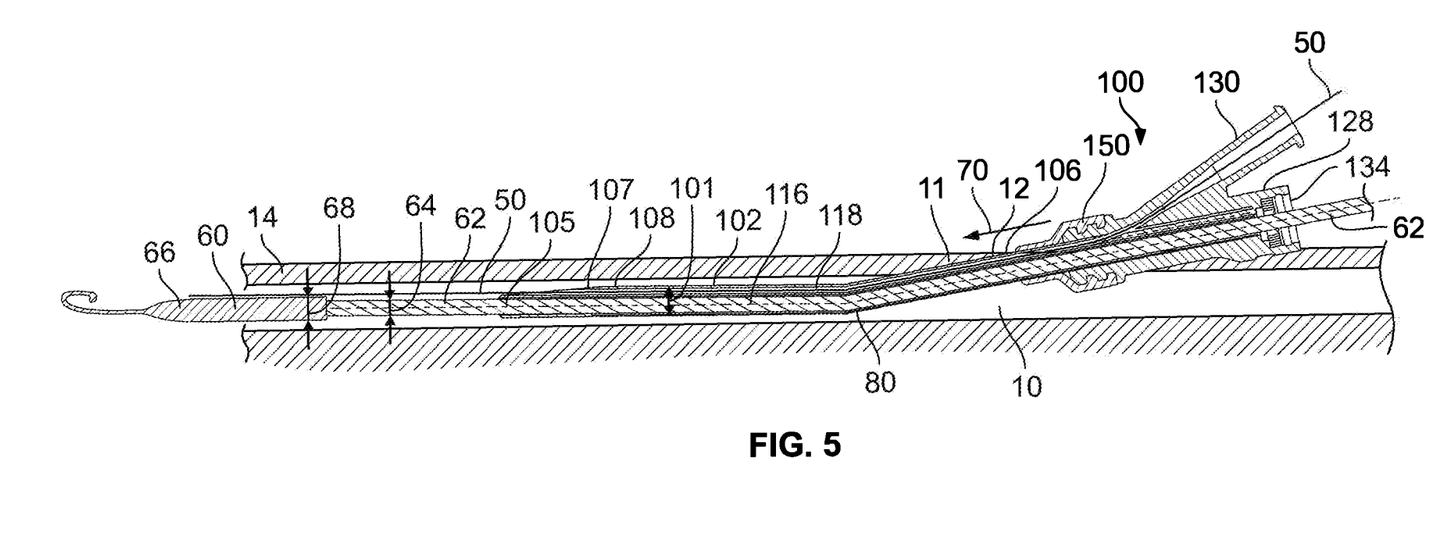
FIG. 5 shows the dual lumen sheath of FIG. 1 inserted into a blood vessel of a patient over a percutaneous pump.

FIG. 5 shows the dual lumen sheath assembly 100 of FIG. 1 inserted into a blood vessel 10 of a patient over a percutaneous pump 60. The percutaneous pump 60 includes a pump head 66 and a catheter body 62. The percutaneous pump 60 may be an intravascular blood pump, a blood pump driven by flexible drive shaft, a blood pump including an implantable motor, a blood pump having an expandable pump rotor, or any other suitable pump. The dual lumen sheath assembly 100 is advanced into the blood vessel 10 over the catheter body 62 of the percutaneous pump 60 through the blood vessel aperture 12 in the direction indicated by arrow 70. The first lumen 116 of the dual lumen sheath assembly 100 may be threaded on the catheter body 62 when the percutaneous pump 60 is initially inserted into the blood vessel 10. The blood vessel 10 may be a femoral artery, and the blood vessel aperture 12 may be an arteriotomy. The blood vessel aperture 12 may have an opening slightly larger than the diameter 64 of the catheter body 62. Thus, the tubular body 102 of the dual lumen sheath assembly 100 may effectively plug the gap between the blood vessel aperture 12 and the catheter by 64 when the sheath assembly 100 is advanced into the blood vessel 10 over the catheter body 62. The outer diameter 101 of the tubular sheath body 102 may be graduated as discussed above to so that the diameter 101 of the tubular sheath body 102 increases from its distal end portion 108 to its proximal end portion 106. This can allow the tubular sheath body 102 to be inserted farther into the blood vessel 10 to plug a larger gap between the blood vessel aperture 12 and the catheter body 62. The plugging effect of the tubular sheath body 102 can reduce or prevent bleeding out of the blood vessel aperture 12. The tubular sheath body 102 is flexible so that the tubular sheath body 102 can form a bend 80 which allows the tubular sheath body 102 to follow the contours of the vessel 10. This flexibility can reduce the stress placed on the blood vessel aperture 12 by reducing the force required to deform the tubular sheath body 102.

Once the tubular sheath body 102 has been advanced over the catheter body 62 of the percutaneous pump 60 to a sufficient depth to plug the gap between the vessel aperture 12 and the catheter body 62, the dual lumen sheath assembly 100 may be fixed relative to the catheter body 62. This fixation may be achieved by fixing the stabilizing structure 150 to the patient's tissue 14. In some implementations, this is achieved by suturing wings (not shown) of the stabilizing structure 150 to the patient tissue 14. In certain implementations, the stabilizing structure 150 is attached to a vascular graft with umbilical tape or sutures. This may be performed during axillary insertions or any other insertions which require pump placement through a vascular graft. In some implementations, fixing the placement of the dual lumen sheath assembly 100 may be achieved by tightening the seal 134 around the catheter body 62 or by means of a separate anchoring ring. The second port 130 may be rotated relative to the stabilizing structure 150 so that the second port 130 lies flat against the patient tissue 14. After the dual lumen sheath assembly 100 has been fixed in the appropriate position, a physician may begin operation of the percutaneous pump 60. The percutaneous pump 60 may be operated during a percutaneous coronary intervention (PCI), open-heart surgery, heart valve replacement surgery, or during treatment of acute myocardial infarction (AMI), cardiogenic shock, or ST segment elevation myocardial infarction (STEMI), as well as any other suitable medical procedure. In certain implementations, the percutaneous pump 60 is operated for an extended period of time, such as greater than six hours, greater than 12 hours, greater than 24 hours, greater than 48 hours, greater than 72 hours, greater than one week, or any other suitable duration of time. In such cases, a stylet (not shown in FIG. 5), such as the stylet 120 from FIGS. 1-4, may be positioned within the second lumen 118 during insertion of the dual lumen sheath assembly 100 to prevent blood ingress into the second lumen 118, which could lead to clotting that could obstruct the second lumen 118 or to bleeding out of the second port 130.

In certain implementations, a pressure bag is connected to the second port 130 in place of the stylet to maintain the patency of the second lumen 118. An infusion pump may be used in combination with the pressure bag to regulate the flow rate of liquid into the patient. For example, the flow rate may be limited to 1 mL/hr, 2 mL/hr, 5 mL/hr, 10 mL/hr, or any other suitable flow rate. In some implementations, a pressure measuring device is connected to the second port 130 to measure the pressure within the vessel 10. This pressure measurement can be used to determine when the second port 130 has been inserted sufficiently deep into the blood vessel aperture 12. For example, when a pressure about equal to arterial pressure is measured at the second port 130, the second outlet 107 may be in fluid communication with the blood vessel 10. After penetration into the blood vessel aperture 12 has been detected, the depth of the blood vessel aperture 12 relative to the patient's skin can be measured using depth markings disposed on an outer surface of the sheath. The measurement of this depth can facilitate the subsequent use of certain vessel closure tools which may require such a measurement. The pressure measurement can also be used to monitor arterial pressure in the blood vessel 10 during a medical procedure. This may allow an arterial pressure measurement to be taken without the use of an additional catheter, which may reduce the amount of equipment necessary in the potentially crowded operating area. Additionally, the second lumen 118 can allow a determination of the depth of insertion without a pressure transducer by allowing observation of the onset of blood flow through the second lumen 118 ("bleedback"), which is indicative of penetration into the blood vessel aperture 12.

When it is time to remove the percutaneous pump 60, a guidewire 50 is inserted through the second port 130 into the second lumen 118 and out the second outlet 107 into the blood vessel 10. Thus, the guidewire 50 enters the same insertion path as the percutaneous pump 60, thereby maintaining access to the insertion path. If a stylet was used during insertion of the dual lumen sheath assembly 100, the stylet is removed before insertion of the guidewire 50. The guidewire 50 has an outer diameter that approximately matches the inner diameter of the second outlet 107 to prevent blood from flowing out of the blood vessel 10 through the second port 130. For example, the guidewire may have an outer diameter of about 1 mm. Additionally, in some implementations, a seal at the second port 130 is included to further ensure that no blood exits the second port 130 while the guidewire 50 is in place.

After the guidewire 50 has been placed in the blood vessel 10, the percutaneous pump 60 and the dual lumen sheath assembly 100 may be removed through the blood vessel aperture 12 while the guidewire 50 is left in place. The tubular sheath body 102 may be coated with a hydrophilic coating or any other suitable coating that prevents adhesions to the blood vessel 10, thereby facilitating removal of the tubular sheath body 102 without damaging the blood vessel 10. The removal of the dual lumen sheath assembly 100 and percutaneous pump 60 while the guidewire 50 is left in place allows guidewire access to the insertion path 11 to be maintained. The removal of the percutaneous pump 60 requires the concurrent removal of the dual lumen sheath assembly 100 because the diameter 68 of the pump head 66 cannot pass through the first lumen 116. This is because the inner diameter of the first lumen 116 is sized to fit tightly around the diameter 64 of the catheter body 62, but cannot accommodate the larger diameter 68 of the pump head 66. As a result, the first lumen 116 is not available to be used to maintain guidewire access to the insertion path 11. Thus, the second lumen 118 is necessary to maintain guidewire access to the insertion path 11.

After the percutaneous pump 60 and the dual lumen sheath assembly 100 have been removed, the guidewire 50 remains in the blood vessel 10 and the insertion path 11. Thus, another tool may be inserted over the guidewire 50 into the insertion path 11. In some implementations, a vascular closure device is inserted into the insertion path 11 using the guidewire 50. The vascular closure device may be the VASOSEAL vascular sealing device, the ANGIO-SEAL bio-absorbable active closure system, the PERCLOSE vascular sealing device, or any other suitable vascular closure device or combination of vascular closure devices. After a vascular closure device or other device has been successfully inserted through the vessel aperture 12 into the insertion path 11, the guidewire 50 may be removed from the vessel aperture 12.

Figure 6:
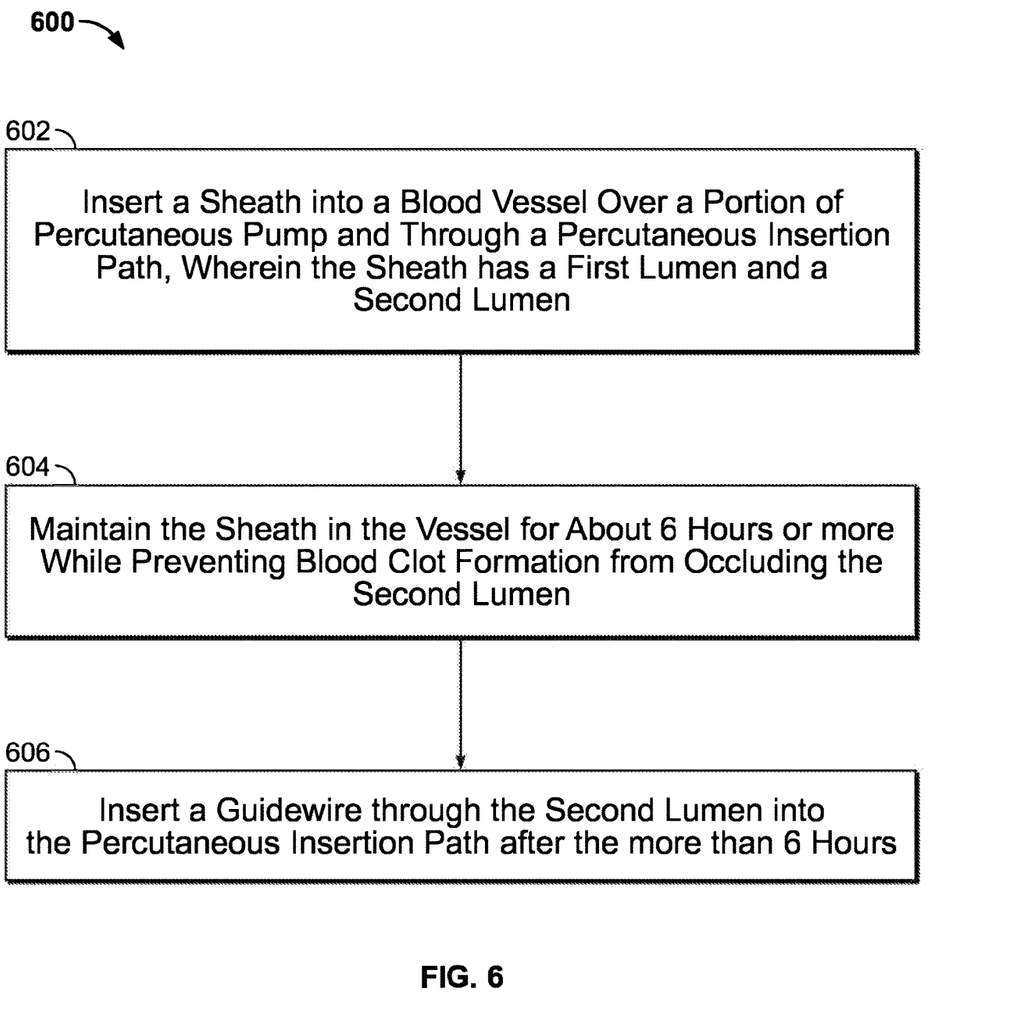
FIG. 6 shows an illustrative process for maintaining guidewire access.

FIG. 6 shows an illustrative process 600 for maintaining guidewire access. The illustrative process 600 may be performed using the dual lumen sheath assembly 100 or any other suitable sheath tool. In step 602, a sheath is inserted into a blood vessel through a percutaneous insertion path and along a portion of a percutaneous pump. The sheath has a first lumen and a second lumen. The blood vessel may be an artery, such as the femoral artery. The insertion path passes through a blood vessel aperture (e.g., an arteriotomy). The percutaneous pump is inserted into the insertion path using an introducer prior to step 602. Therefore, the percutaneous pump guides the sheath into the existing insertion path. The percutaneous pump may be an intravascular blood pump, a blood pump driven by flexible drive shaft, a blood pump including an implantable motor, a blood pump having an expandable pump rotor, or any other suitable pump. The first lumen of the sheath may be sealed against the percutaneous pump by a hemostatic valve to prevent leakage of blood from the blood vessel out of the patient.

In some implementations, the sheath is only inserted into the vessel as deep as is necessary to close the gap between the percutaneous pump and the vessel aperture to prevent bleeding. To reliably detect whether the sheath has been inserted sufficiently deep into the vessel, the pressure within the vessel can be detected using the second lumen. For example, a detected pressure about equal to arterial pressure may indicate that the outlet of the second lumen has been inserted into the blood vessel. Alternatively, the second lumen can allow a determination of the depth of insertion without a pressure transducer by allowing observation of the onset of blood flow through the second lumen ("bleed-back"), which is indicative of penetration into the blood vessel aperture. After penetration into the blood vessel aperture has been detected, the depth of the blood vessel aperture relative to the patient's skin can be measured using depth markings disposed on an outer surface of the sheath. In some implementations, the depth markings are radio-opaque and can be imaged using a tomographic imaging modality (e.g., CT, MRI, X-ray). The measurement of this depth can facilitate the subsequent use of certain vessel closure tools which may require such a measurement. Additionally, once inserted to the appropriate depth, the second lumen can be used to measure arterial pressure during the procedure.

In step 604, the sheath is maintained in the vessel for about six hours or more while blood clot formation is prevented from occluding the second lumen. The sheath may be maintained in the vessel for 6 hours, 12 hours, 24 hours, 48 hours, 72 hours, one week, two weeks, or any other suitable duration of time. Blood clot formation in the second lumen may be prevented during this time using a stylet that temporarily occludes the second lumen. For example, the stylet 120 of FIGS. 1-3 may be used to temporarily occlude the second lumen. In certain implementations, blood clot formation in the second lumen is prevented or reduced using a drug or nondrug coating in the second lumen. The coating may include heparin or any other suitable substance. In some implementations, blood clot formation in the second lumen is prevented or reduced by flushing the second lumen with a liquid (e.g., saline solution, glucose solution, or any other suitable solution). Preventing the occlusion of the second lumen by blood clots allows the patency of the second lumen to be preserved for insertion of a guidewire.

In step 606, a guidewire is inserted through the second lumen into the percutaneous insertion path after the about six hours or more. If a stylet was used to temporarily occlude the second lumen, the stylet is removed before inserting the guidewire. The percutaneous pump inserted through the first lumen may be removed after insertion of the guidewire. After the guidewire has been inserted, the sheath may be removed from the percutaneous insertion path while the guidewire remains in place. This can allow another tool (e.g., an access closure tool) to be inserted into the insertion path. This frees a physician from depending on an introducer to maintain guidewire access. Thus, the physician is able to remove the introducer earlier in a procedure. This can allow greater recoil of the blood vessel aperture, thereby reducing the risk of bleeding. For example, removing the introducer within an hour of insertion may allow a recoil of about 2 to 3 Fr (0.667 mm to 1 mm).

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system percutaneous intravascular blood pumps, may be applied to systems, methods, and devices for other implantable blood pumps or implantable cardiac assist devices.

Variations and modifications will occur to those of skill in the art after reviewing this disclosure. For example, in some implementations, the sheath assembly may be used to provide guidewire access for procedures of a short duration (e.g., less than six hours). Furthermore, the stylet may be omitted in some implementations in which the patency of the second lumen is adequately maintained by other means. For example, in some implementations, the second lumen is flushed with a liquid, either intermittently or continuously. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method comprising the steps of:
    inserting a percutaneous pump into a blood vessel of a patient;
    while the percutaneous pump is in the patient, inserting a sheath into the blood vessel through which the percutaneous pump was inserted, wherein the sheath has a first lumen and a second lumen;
    advancing the sheath over a catheter body of the percutaneous pump such that the catheter body is in the first lumen; and
    maintaining patency of the second lumen while the catheter body is in the first lumen and the sheath is in the blood vessel for more than 6 hours.

2. The method of claim 1, further comprising operating the percutaneous pump for more than 6 hours.

3. The method of claim 1, wherein the sheath is inserted into the blood vessel via an aperture in the blood vessel.

4. The method of claim 3, wherein the sheath is advanced over the catheter body until a gap between the aperture in the blood vessel and the catheter body is plugged.

5. The method of claim 4, further comprising fixing a position of the sheath relative to the catheter body using a support structure.

6. The method of claim 5, wherein fixing the position of the sheath comprises tightening a seal around the catheter body or using an anchoring ring.

7. The method of claim 1, wherein maintaining patency of the second lumen comprises flushing the second lumen with a purge fluid or applying a drug coating or a nondrug coating to the second lumen.

8. The method of claim 7, further comprising inserting a guidewire into the second lumen while the percutaneous pump is in the patient.

9. The method of claim 1, wherein maintaining patency of the second lumen comprises inserting a stylet into the second lumen.

10. The method of claim 1, further comprising inserting a stylet into the second lumen during insertion of the sheath into the blood vessel, such that the stylet substantially occludes the second lumen.

11. The method of claim 10, further comprising operating the percutaneous pump for more than 6 hours.

12. The method of claim 10, further comprising removing the stylet from the second lumen while the percutaneous pump is in the patient.

13. The method of claim 12, further comprising inserting a guidewire into the second lumen after the stylet is removed and while the percutaneous pump is in the patient.

14. The method of claim 13, further comprising removing the percutaneous pump through the first lumen and an aperture in the blood vessel.

15. The method of claim 14, further comprising removing the sheath through the aperture in the blood vessel, such that the guidewire remains within the blood vessel.

16. The method of claim 15, further comprising inserting a percutaneous tool over the guidewire in the blood vessel after the sheath is removed.

17. The method of claim 1, wherein the second lumen comprises a proximal inlet and a distal outlet, and wherein the method further comprises:
    coupling a sensor to the proximal inlet of the second lumen; and
    transducing arterial pressure at the distal outlet of the second lumen using the sensor.

18. The method of claim 17, wherein the method further comprises rotating the sheath relative to a support structure when an arterial pressure measurement indicates that the distal outlet of the second lumen is occluded by an arterial wall.

19. The method of claim 18, further comprising determining a depth of insertion from the arterial pressure measurement.

20. The method of claim 19, wherein the depth of insertion is determined based on markings disposed on an outer surface of the sheath.

* * * * *